(12) United States Patent
Thomas et al.

(10) Patent No.: US 8,712,716 B2
(45) Date of Patent: Apr. 29, 2014

(54) CIRCUITRY FOR MEASURING AND COMPENSATING PHASE AND AMPLITUDE DIFFERENCES IN NDT/NDI OPERATION

(75) Inventors: Andrew Thomas, Westford, MA (US); Marc Dulac, Dracut, MA (US)

(73) Assignee: Olympus NDT inc., Waltham, MA (US)

( * ) Notice: Subject to any disclaimer, the term of this patent is extended or adjusted under 35 U.S.C. 154(b) by 451 days.

(21) Appl. No.: 13/194,568

(22) Filed: Jul. 29, 2011

(65) Prior Publication Data

US 2013/0030726 A1   Jan. 31, 2013

(51) Int. Cl.
*G06F 19/00* (2011.01)
(52) U.S. Cl.
USPC .............................. 702/104; 702/69; 702/106
(58) Field of Classification Search
USPC ........... 702/56, 69, 72, 85, 89, 103–106, 116, 702/124; 73/602
See application file for complete search history.

(56) References Cited

U.S. PATENT DOCUMENTS 8,408,061 B2 * 4/2013 Thomas .......................... 73/602

* cited by examiner

*Primary Examiner* — Manuel L Barbee
(74) *Attorney, Agent, or Firm* — Ostrolenk Faber LLP

(57) ABSTRACT

Disclosed are a method and an NDT/NDI inspection device deploying digital circuitry to conduct detection and compensation of phase and amplitude shift in responding signals. A digital waveform generator, such as a direct digital synthesizer (DDS) is used to generate a digital sine-wave of a specific frequency and amplitude, mimicking the pulser frequency and amplitude. The sine-wave is converted to analog signal through a DAC and transmitted to the transducer. The received analog sine-wave from the transducer is converted back to a digital signal through an ADC. The transmitted and received digital signals are then compared for phase and amplitude differences. A null circuit involving another waveform generating component is employed to compensate the detected phase and amplitude differences. As a result the phase and amplitude differences are effectively eliminated before being further processed and analyzed for defects information.

21 Claims, 5 Drawing Sheets

CIRCUITRY FOR MEASURING AND COMPENSATING PHASE AND AMPLITUDE DIFFERENCES IN NDT/NDI OPERATION

FIELD OF THE INVENTION

The present invention relates to non-destructive testing and inspection devices (NDT/NDI) and more particularly to an NDT/NDI device with improved phase and amplitude measurement and compensation using a digital circuit.

BACKGROUND OF THE INVENTION

During NDT/NDI operations, detecting or transmitting signals are sent into targeted test objects. Responding signals are received by the instrument or system of the NDT/NDI operation, back from the test objects. In many applications, the characteristics of the detecting signals involve amplitude and phase. However, the amplitude and phase of the responding signals often shift from their original detecting ones due to reasons that are not associated with the defects or thickness of the test objects. The shift in the responding signal's amplitude and phase in comparison to those of the original detecting signals can be attributed to factors including certain intrinsic properties of the circuitry of the probes used by the NDT/NDI operation, or the material of the test objects. Quantifying and compensating for this type of phase and amplitude shift have become significantly important to the inspection accuracy since the defects can be better isolated when the shift of the phase and amplitude caused by intrinsic factors are removed.

Phase and amplitude detection in NDT/NDI is typically used for measuring thickness and detecting flaws in various materials. The variations of phase and/or amplitude of the received alternating current (AC) signal from the transmit signal caused by the test piece determines the thickness or presence of a flaw in the material. A null circuit is also necessary to null out (subtract) phase and/or amplitude differences caused by elements other than the desired test piece such as the probe and electrical circuitry. Conventional NDT/NDI inspection or measurement systems employ mostly analog methods to perform phase and amplitude detection of a received electrical waveform from a detecting transducer. The mostly analog methods require many analog components which can induce higher noise levels and have higher temperature drift effects in the test system thereby creating larger errors in the inspection results.

Another typical problem associated with mostly analog versus digital methods of phase and amplitude detection is that it requires multiple components thereby increasing the cost of the inspection or measurement system and requiring a larger amount of printed circuit board area making the inspection or measurement system larger while digital methods can be compacted into a single field programmable gate array (FPGA), CPLD or other programmable digital device.

Ideally digital methods of phase and amplitude detection are desired due to the fact that they impose lower noise errors on the inspection and measurement results of the test piece while requiring less printed circuit board area creating smaller and therefore lower cost inspection or measurement systems.

To overcome the problems attributed to using traditional mostly analog circuitry to conduct the phase and amplitude difference, the present application presents a method and circuitry to use digital components to achieve phase and amplitude detection and compensation. The use of programmable digital devices provides many advantages including allowing for reprogram-ability of the circuit for field upgrades and new circuit configurations. Also disclosed in the present application is a digital null circuit which replaces a conventional analog null circuit which uses a larger number of components for finite compensation of phase and amplitude difference in the transducer and electrical circuit while the presently disclosed digital methods can give near infinite compensation.

The waveform generator and digital null circuit in the present disclosure employ, among other components, a digital waveform generator such as a direct digital synthesizer, known in the industry as a 'DDS'. Other existing efforts have been found to use DDS components in NDT/NDI devices for measuring electrical impedance of transducers and the conductive targets. However in this disclosure, these existing methods using digital waveform generators in NDT/NDI devices are utilized either in a different manner or to resolve different problems that are not of concern to the present disclosure.

U.S. Pat. No. 6,703,843 (herein later as '843) discloses a digital eddy current proximity system for digitally measuring the proximity probes impedance correlative to displacement and position of the metallic target being monitored.

The U.S. Pat. No. 6,703,843 patent shows multiple discrete DDS devices for waveform generation and a discrete DSP for impedance measurement. This disclosure uses a single FPGA, CPLD or other programmable digital device with embedded DDS for signal generation and waveform measurement of phase and amplitude in a single device which is an improvement over using multiple discrete DDS and DSP devices.

More specifically, '843 calculates electrical impedance of the probe by determining a voltage 1 and a voltage 2 across a resistance means. However, the present disclosure calculates phase and amplitude by transmitting a high energy electrical waveform into a transducer which is coupled into the test piece and receives the electrical sine-wave from the transducer through the test piece to determine phase and amplitude differences from the original transmit waveform. Returning to the problem at issue, '843 does not provide a solution for detection of phase and amplitude differences.

The same inventor teaches in U.S. Pat. No. 6,850,077 a solution to a problem similar to that of the '843 patent and therefore does not provide a solution to the problem of the present disclosure.

Thus, given the problems attributed to the mostly analog approach and the lack of digital solution solving the subject problem herein discussed, a digital circuit and method for measuring and compensating phase and amplitude difference in electrical and acoustical signals in NDT/NDI devices is disclosed as follows.

SUMMARY OF THE INVENTION

The invention disclosed herein solves the problem related to the detection of phase and amplitude differences in detecting and responding signals used in NDT/NDI devices such as eddy current inspection, bond testing, Hall-effect (magnetic) measurement and other various acoustical and electrical measurement systems where the existing method using mostly analog circuitry for phase and amplitude difference presents the aforementioned drawbacks, such as undesirable noise and sensitivity to temperature drift effects in the measurement results.

It should be noted that NDT/NDI devices that can benefit from using the present disclosure include any device, in which, phase and amplitude differences exist in the detecting and responding signals. Such devices include eddy current inspection, bond testing, Hall-effect (magnetic) measurement and other various acoustical and electrical measurement devices with either single or array element transducers. Also should be noted is that the terms "probe", "transducer", and "sensor" herein used may be used interchangeably and include the cable from the NDT/NDI device.

Accordingly, it is a general object of the present disclosure to provide a method and an NDT/NDI inspection device capable of detecting phase and amplitude differences of an electrical or acoustical signal with desirable accuracy without causing excessive noise and temperature drift.

It is further an object of the present disclosure to provide a method and circuitry to use programmable digital components to achieve phase and amplitude detection in NDT/NDI devices to allow reprogram-ability of the circuit for field upgrades and new circuit configurations.

It is further an object of the present disclosure to utilize a digital null circuit to replace a conventional analog null circuit.

It is yet another object of the present disclosure to conduct phase and amplitude difference detection without the usage of a large number of analog components.

It is further an object of the present disclosure to provide a method and circuitry capable of providing near infinite compensation of phase and amplitude difference in the transducer and circuit.

It can be understood that the presently disclosed method and circuitry provide the advantages of providing infinite compensation of phase and amplitude difference without using a large number of electronic (analog) components.

It also should be appreciated that the presently disclosed circuitry provides the advantanges of lower development cycle and reduced manufacturing cost.

In addition, an alternative embodiment of the presently disclosed probe provides the advantage of achieving lower signal to noise ratios and lower temperature drift effects which are desirable characteristics for NDT/NDI devices to possess.

DETAILED DESCRIPTION OF PREFERRED EMBODIMENT

The measurement of phase and amplitude is continuously monitored for differences between responding signals and transmit (detecting) signals by continuously injecting a transmit signal into the test piece and monitoring the responding signal from the test piece. A herein disclosed null compensation is done once during a calibration session before measurement with the transducer un-coupled from the test piece, to compensate for phase and amplitude differences caused by system and test piece's intrinsic properties such as the transducer and electrical circuitry.

It should be noted that when referring to numerals of items in the figures, a numeral without a post-suffix is meant to denote all items in the figure that bear the same numeral with a post suffix. For example, digital waveform generator 10 shown in FIGS. 1 and 2 is meant to denote all and each waveform generator of the same kind, namely 10-1, 10-2, and so on.

It should be noted that the present disclosure presents a design that relates to different technologies used for non destructive testing (NDT) such as eddy-current, bond-testing, Hall-effect and other various technologies that use a transducer to transmit an electromagnetic or acoustical waveform to monitor defects such as bond malformation, cracks, voids and thickness measurements of the test piece. During NDT inspection using the method or device according to the present disclosure, an AC (alternating current) electrical waveform (sine wave) is transmitted from waveform generator 10 which sends out a signal of specific frequency and amplitude to the transducer which in turn generates an electromagnetic or acoustical signal in which its phase and amplitude are altered by the test piece. The baseline frequency and amplitude of the signal going to transducer 50 are determined by the specific test piece material being inspected (such as type, thickness and density of the material).

Figure 1:
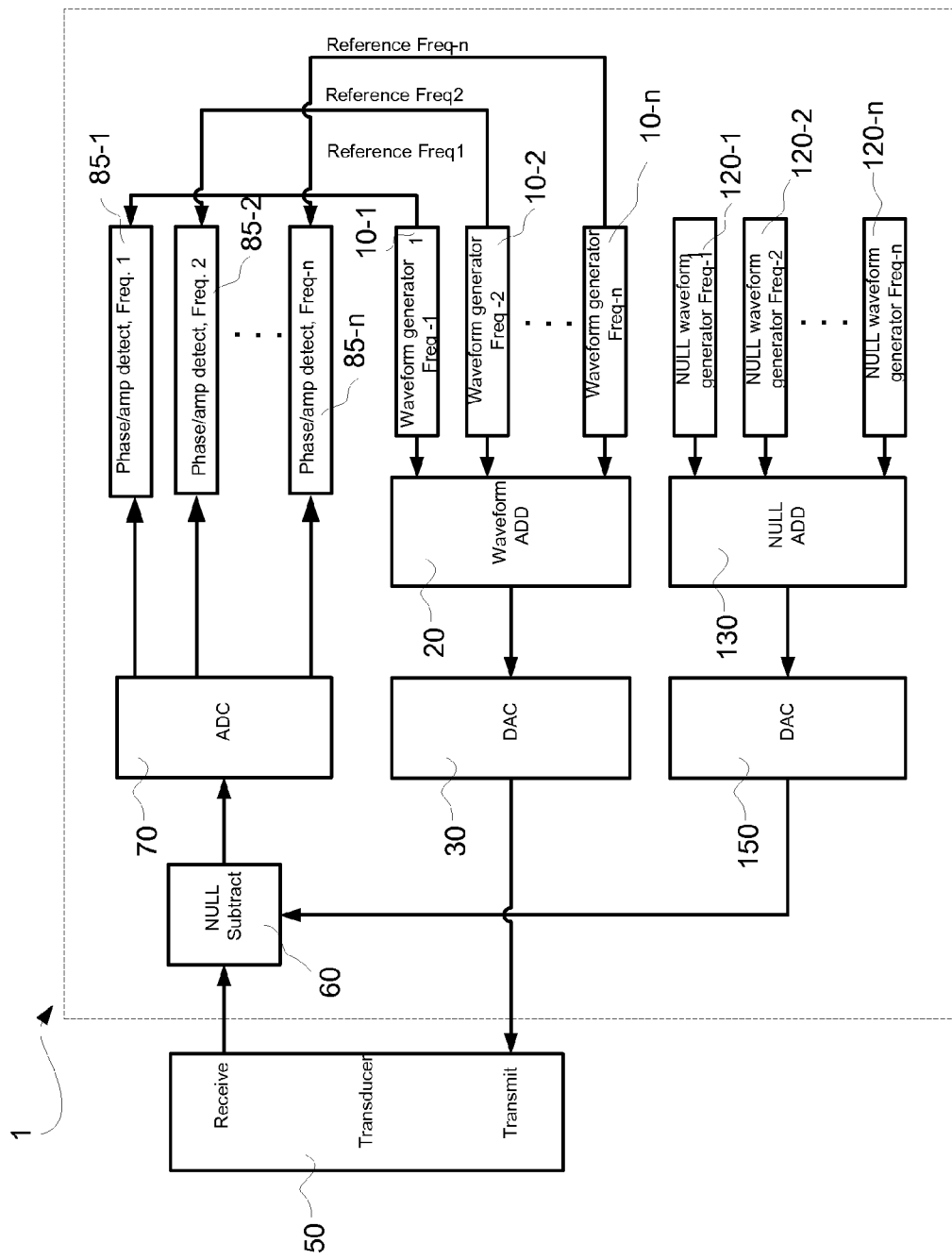
FIG. 1 is a simplified diagram that illustrates the presently disclosed method and circuitry employed to perform phase and amplitude detection and compensation.
Figure 2:
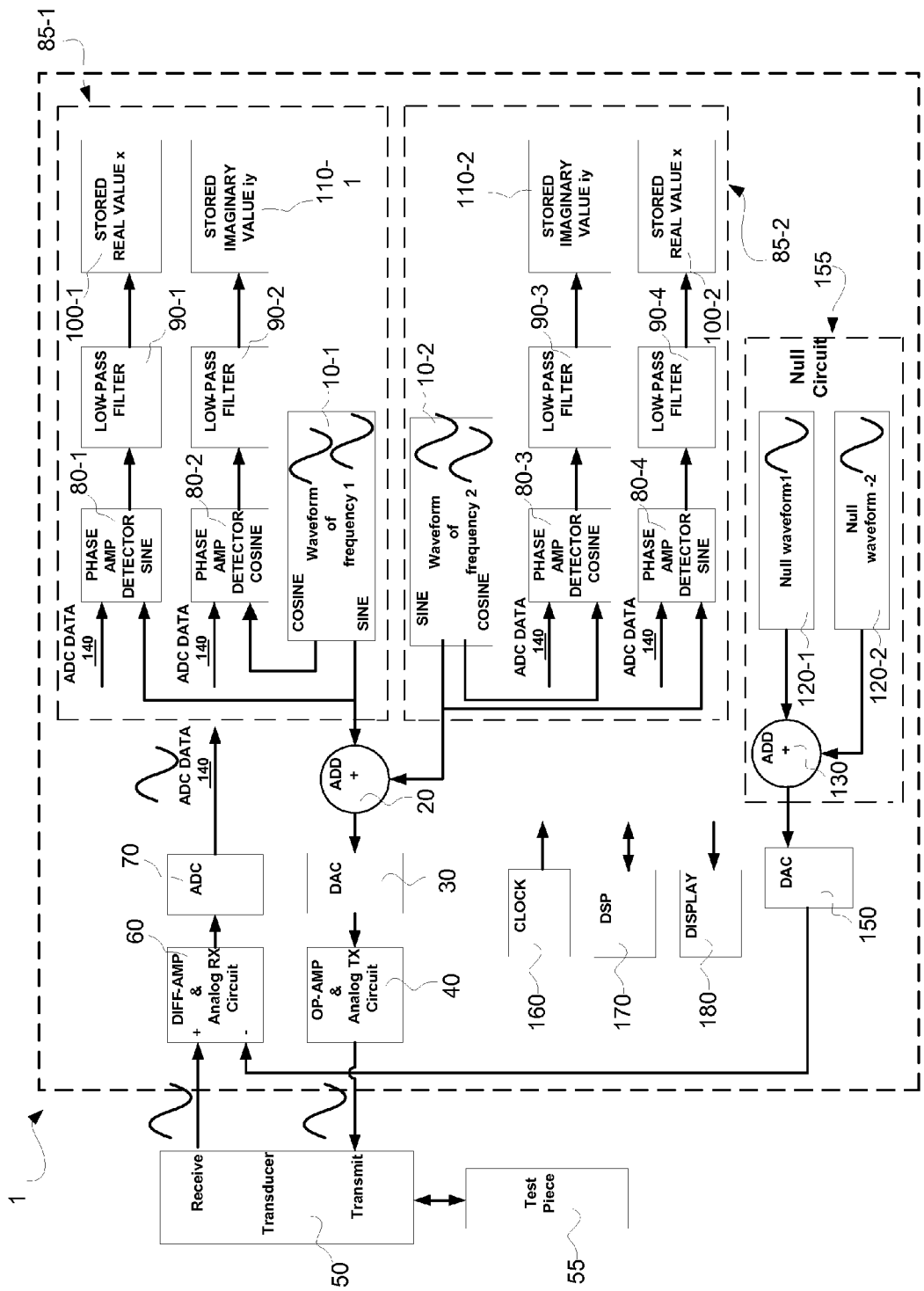
FIG. 2 is a schematic diagram providing more details of the digital waveform generator and null circuits which are used to perform phase and amplitude detection according to the present disclosure.

Referring to FIG. 1, during an NDT/NDI inspection, a transducer 50 receives an electrical waveform in responding signals and produces an electromagnetic or acoustical signal the phase and amplitude of which are altered by a test piece (55 in FIG. 2), to produce an electrical signal on the receive side of the transducer 50. The received electrical signal is monitored for phase and amplitude changes through a digital phase and amplitude detection circuit 1 according to the present disclosure.

Single, dual or multiple waveforms of signals of different frequencies can be received for phase and amplitude detection in single mode, dual mode or multi mode, respectively. Depending on the mode of application, one or more digital waveform generators, 10-1 and 10-2 are configured to generate waveforms such as waveform-1 and waveform-2, respectively, each of which pertains to predetermined baseline frequencies. The waveform generators can be in the form of Direct Digital Synthesizer (herein as DDS). The waveforms are subsequently added together by an adder 20 to form a single waveform that is transmitted to the transducer 50 through a DAC (Digital to Analog Converter) 30. The waveforms (waveform-1 and waveform-2) that are generated by waveform generators 10 and transmitted are also re-serviced as reference signals to be compared against the received signal for each specific frequency.

It should be noted that when multiple baseline frequencies, such as frequency 1 and frequency 2 are employed, waveform-1 and waveform-2 are herein defined as waveforms of frequency 1 and waveforms of frequency 2, respectively. Waveform-1 and waveforms of frequency 1 are interchangeably used in the present disclosure. It applies to all generated waveforms of other predetermined frequencies.

The received waveform from transducer 50 is converted to digital data 140 through the ADC (Analog to Digital Converter) 70 for phase and amplitude detection of each waveform of specific frequency using the reference signals generated by waveform generators 10.

A digital null circuit, such as 155 is employed to compensate or null out any inherent phase and amplitude differences caused by the transducer and subsequent circuitry. Digital null circuit 155 has digital waveform generators 120 which are used to vary its phase and amplitude value that will null or zero out any phase and amplitude errors caused by the transducer and electrical circuit when the transducer is un-coupled from the test piece. The varied phase and amplitude values obtained during the null process are used to compensate for the phase and amplitude differences of transducer 50 and electrical circuit during measurement of the test piece.

It should be noted that waveform generators 120, depending on the specific design preference, can be the same as waveform generators 10. In another word, the same waveform generators, which can be implemented in devices such as an FPGA, can perform the dual functions provided by waveform generators 10 and 120, and such design variation is within the scope of the present disclosure.

Reference is now turned to FIG. 2, which elaborates on FIG. 1 with a detailed description of a preferred embodiment of the digital phase and amplitude detector with null circuit compensation provided.

It should be noted that the two major novel aspects of the present disclosure include phase and amplitude detection and compensation.

Concerning the aspect of conducting phase and amplitude detection, according to FIG. 2, an exemplary embodiment of the present disclosure involving processing a dual mode waveform and detecting phase and amplitude difference of such is described.

There are three different modes of phase and amplitude detection covered in the present disclosure which are single, dual and multi modes. The selection of mode is made based on the NDT/NDI methods of flaw detection and on various applications. Single mode will transmit a single waveform while dual mode will transmit two added waveforms of specific frequency and amplitude to the test piece. As an example, eddy current methods of inspecting for flaws may involve single or dual modes; bond testing and Hall-effect measurement often involve single mode. A dual mode is presented as an exemplary case to show that multiple waveforms of different frequency and amplitude can be added and transmitted to the test piece based on specific requirements for specific applications.

As seen in FIG. 2, a dual mode phase and amplitude detection circuit 1 is configured to have two waveform generators and detection circuits 85-1 and 85-2 associated with waveform-1 and waveform-2, respectively. It should be noted that for single mode waveform-1, generator and detection circuit 85-1 is used while waveform-2 is zeroed out (not used). For multi mode with both waveform-1 and waveform-2 involved, signal generator and detection circuits 85-1 and 95 are both used while adding multiple waveform blocks such as waveform-1 and waveform-2 through adder 20. Waveform generator 10 generates an AC electrical waveform, such as a sine wave, according to specific baseline frequency and amplitude to adder 20. This waveform is purposed to be generated as the digital version of the original transmitting or detecting signal sent to the test piece 55 according with corresponding predetermined baseline frequency.

Waveform generators 10 also provide a waveform reference signal such as sine (0 degrees) and cosine (90 degrees) waveform to the phase and amplitude detectors 80 for the real and imaginary phase and amplitude reference values. Adder 20 adds two waveforms waveform-1 and waveform-2 generated respectively by the generator circuits 85-1 and 85-2 of different frequencies and amplitudes for dual mode to form a single waveform to be sent to DAC 30. The use of dual and multi mode allows the test piece 55 to be tested with different frequencies concurrently.

Still remaining on the aspect of phase and amplitude detection, continuing with FIG. 2, DAC 30 is a digital to analog converter which converts the digital waveform into an analog signal, which is sent to an analog operational amplifier (op-amp) and analog transmit circuit 40 for gain and offset adjustment. The op-amp and analog transmit circuit 40 is adjusted for gain and offset based on the specific application and type of transducer 50. Transducer 50 takes an electrical waveform on the transmit side from the op-amp 40 and produces an electromagnetic or acoustical signal in which its phase and/or amplitude are altered by the test piece 55 due to its thickness or having a crack, bond malformation, void or other anomaly in its structure. Transducer 50 produces an electrical waveform of shifted phase and/or amplitude on the receive side based on the test piece 55 and sent to a differential amplifier and analog receive circuit 60. Differential amplifier and analog receive circuit 60 is used to set the gain of the received electrical waveform and determine the null or zero value of any inherent phase and amplitude difference derived from the transducer element and circuitry when not coupled to the test piece 55.

Null circuit 155 feeds the negative side of differential amplifier 60 through a digital to analog converter 150 and is used to subtract or compensate for varying phase and amplitude of the transducer and circuitry by using a waveform (sine wave) of varying phase and amplitude from waveform generators 120.

Continuing with FIG. 2, differential amplifier and analog receive circuit 60 feeds ADC 70 which is an analog to digital converter used to convert the analog waveform to digital data 140 in order to detect the phase and amplitude digitally. Digital data 140 is supplied to phase and amplitude detectors 80-1 and 80-2 for single mode case, and further to phase and amplitude detectors 80-3 and 80-4 for dual mode case. Phase and amplitude detectors 80 digitally multiply the ADC waveform carried by ADC data 140 to a sine and cosine reference waveform from digital waveform generator 10 to determine phase and amplitude of the real and imaginary values.

Figure 4:
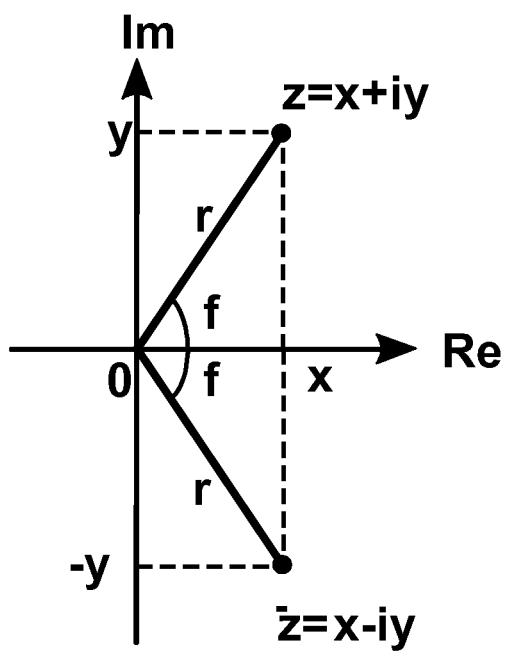
FIG. 4 is a diagram of a complex plain showing how the phase angle and amplitude of the received waveform are calculated according to the present disclosure.

Reference is now made conjunctionally to FIG. 4 and FIG. 2. Phase and amplitude detectors 80 preferably feed the digital low-pass filter block 90 to filter out the high frequency elements of the multiplied waveform while retaining the low frequency elements. The filtered waveform for the calculated real value X is stored in a memory 100 and the calculated imaginary value Y is stored in another memory 110. The stored real X and imaginary Y values are quantified representation of the phase and amplitude difference between the responding waveforms and generated waveform-1 and waveform-2, respectively. In multi mode there can be multiple waveform blocks such as waveform-1 85-1 and waveform-2 85-2 that will have stored real x and imaginary y values to determine phase and amplitude for each waveform.

FIG. 4 shows a diagram of the complex plane. It illustrates how the phase angle and amplitude of the received waveform are calculated using the sine (0 degree real) and cosine (90 degree imaginary) reference for phase and amplitude detection. The real part of a complex number z=x+iy is x and the imaginary part is y. The phase and amplitude difference is therefore calculated according to Eq. 1 and 2 as follows.

$$\text{Phase Angle} = \text{ARC TAN}(\text{imaginary}(iy)/\text{real}(x)) \quad \text{Eq. 1}$$

$$\text{Amplitude} = \text{real}(x) \quad \text{Eq. 2}$$

Accommodating the dual mode embodiment, as an exemplary case for multi-mode, null circuit 155 utilizes two digital waveform generators 120-1 and 120-2 that are waveform generators which produce two null waveforms with adjustable phase and amplitude for null compensation, respectively for frequencies of waveform-1 and waveform-2. Null circuit 155 as shown can support single or dual frequency modes which are added by the add block 130 to generate a single electrical waveform (sine wave) of a specific frequency, phase and amplitude. Similarly, additional null waveform generators, such as 120-1 and 120-2 can be added to support multi frequency mode null using a larger add block 130. The frequencies of the null waveform generators 120 are set to the same frequency as the waveform-1 and waveform-2 generated by waveform generators 10-1 and 10-2 respectively. The null waveform generators 120-1 and 120-2 are adjusted to compensate for the transducer and circuit's phase and amplitude difference for each frequency respectively. Adder 130 feeds DAC 150 to convert the waveform from digital to analog. Also similarly to single mode embodiment, DAC 150 feeds a differential amplifier 60 to subtract the inherent phase and amplitude difference of the transducer and circuit.

It should be appreciated that it is within the scope of the present disclosure as to how the herein disclosed digital circuitry and method are implemented by industry available microprocessors or programmable digital devices. Optionally, circuitry 110 as shown in FIG. 2 can be implemented by a FPGA, CPLD or other programmable digital device. Further optionally, a digital signal processor (DSP) or other type of processor can be used to extract the real and imaginary data from memory 100 and 110, to calculate phase and amplitude and send it to a display 180 for visual monitoring of phase and amplitude. A clock 160 is used to clock the digital logic in the FPGA 110, CPLD or other programmable digital device for processing of the data.

Further optionally, circuitry 110 can share an FPGA with other existing elements of digital circuitry that are used conventionally by existing NDT/NDI devices.

Description of an Alternative Embodiment

Figure 3:
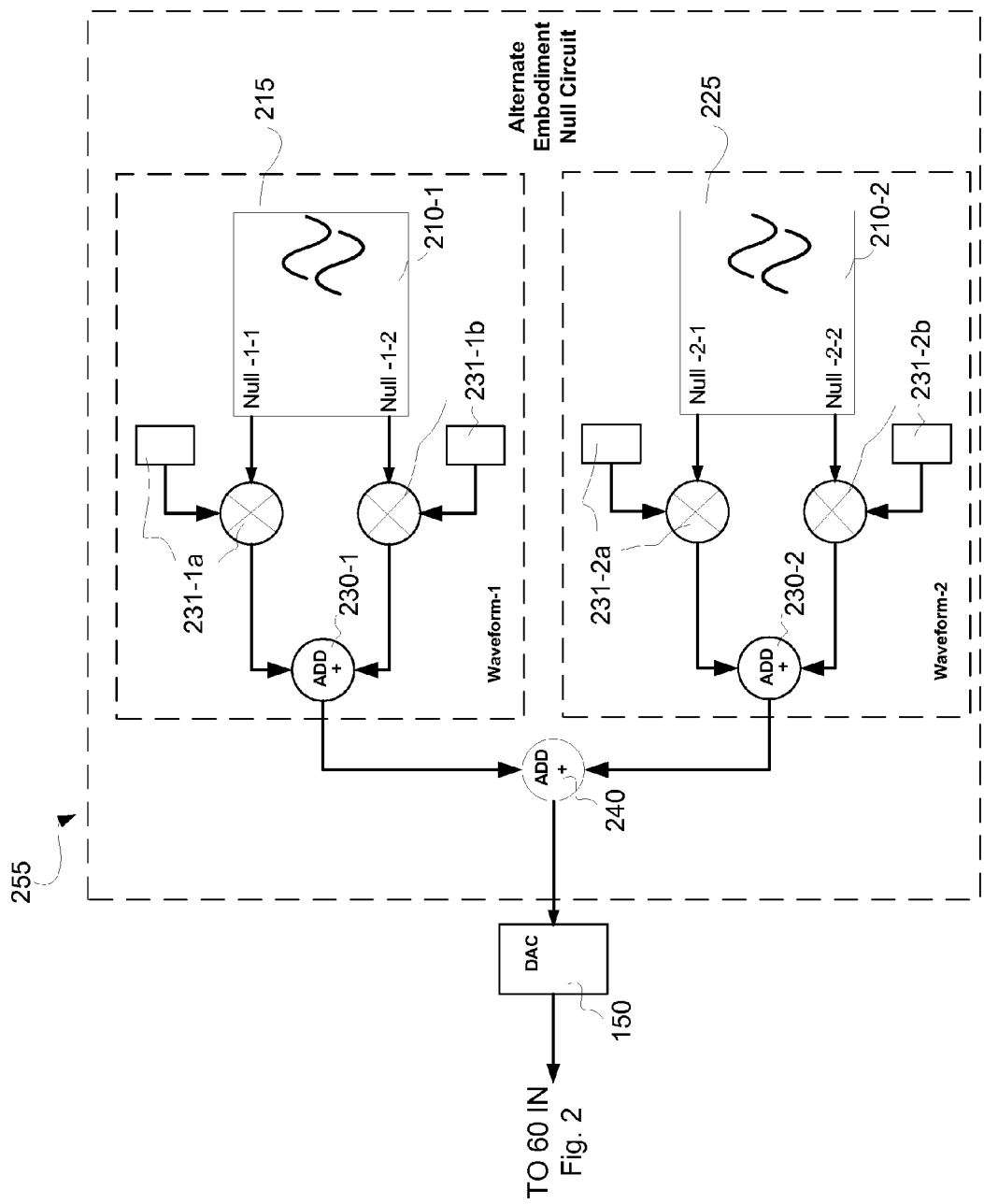
FIG. 3 presents an alternative null circuit embodiment according to the present disclosure.

Depicted in FIG. 3 is a null circuit 255 as an alternative of null circuitry 155 of the preferred embodiment. It should be noted that the entire description of the preferred embodiment applies to this alternate embodiment and should be construed in a complementary manner. Null circuit 255 is provided to substitute null circuitry 155 to form an alternative embodiment.

As can be seen in FIG. 3, null circuit 255 is configured to generate two digital waveforms orthogonal to each other by a digital waveform generator 210-1 to produce the real and imaginary parts which are subsequently adjusted by amplitude controls 231-1*a* and 231-1*b*, respectively. The resulting null waveforms are then added by an adder 240 for phase and amplitude compensation of the transducer and circuitry. In FIG. 3, two exemplary waveforms are shown for dual frequency mode with the understanding that more than two (multiple) waveforms such as 215 and 225 can be added with a larger add 240 block for multi frequency mode.

Continuing with FIG. 3, the orthogonal waveform generator produces the real and imaginary values that are added together by the add block 230 to form a single sine wave with real and imaginary parts. Using real and imaginary values allows for finer adjustment for null circuit 255 while using additional adders 230 as compared to the preferred embodiment. Waveform generators 210 can be adjusted for phase, amplitude and frequency to null and compensate for varying phase and amplitude of the transducer and circuit. The real and imaginary part of the two waveforms produced by null waveform generating circuits 215 and 225 are later added together by an adder 240 to support the null process for dual frequency mode. Multiple waveform blocks such as 215 and 225 can be implemented to support a multiple frequency mode null with a larger add block 240 in a similar fashion.

Description of Operational Steps

Figure 5:
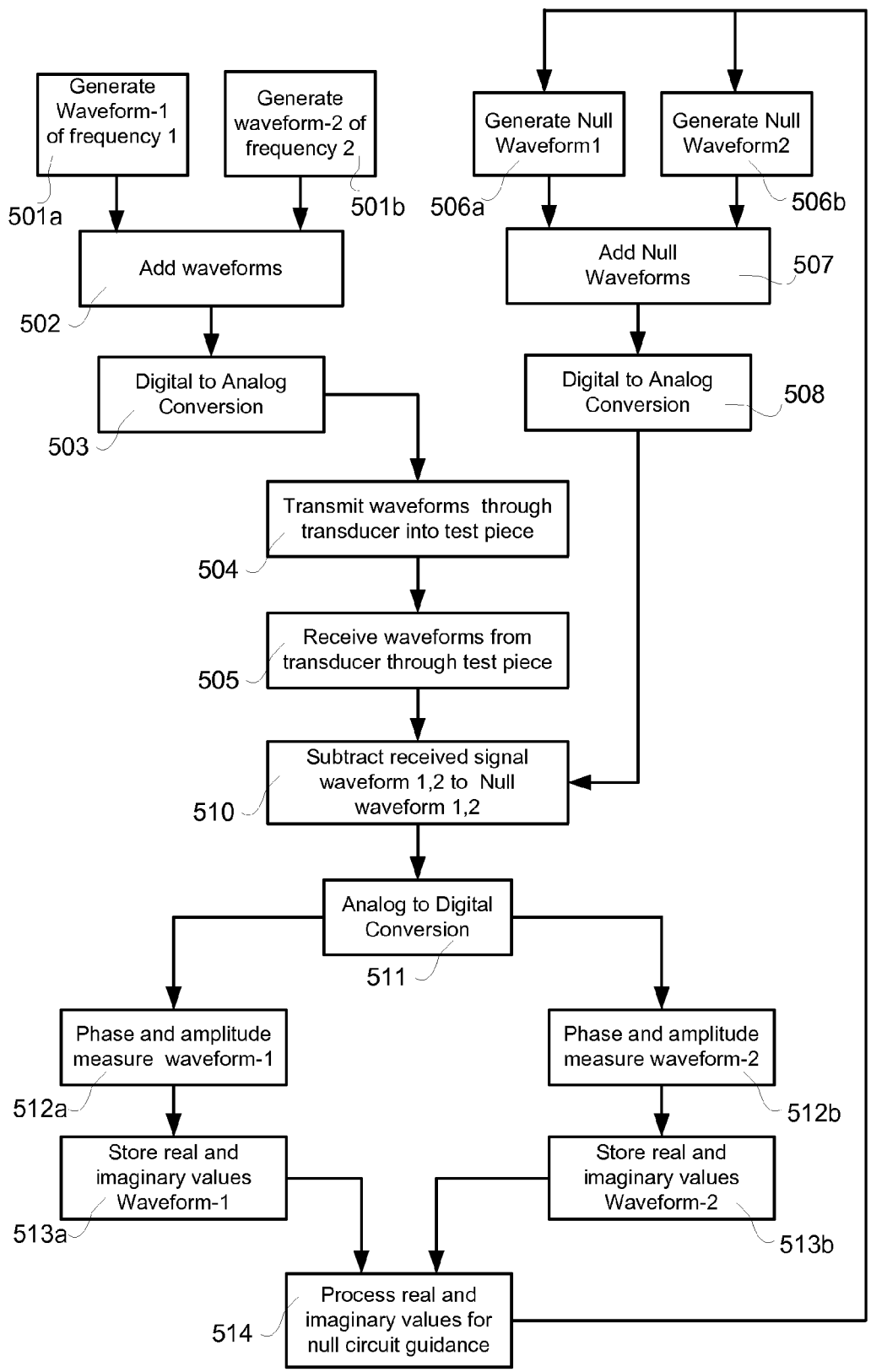
FIG. 5 is a flowchart diagram showing the execution steps used in the presently disclosed phase and amplitude detection and measurement process.

Reference is now made to FIG. 5, which illustrates signal processing steps during a NDT/NDI instrument calibration sessions wherein the disclosed design for phase and amplitude difference compensation is employed.

It should be noted that such calibration process is normally carried out when there is a change of a probe or transducer and/or change of the type of test object. The process should be performed on test pieces with known physical properties that are free of defects.

It should be appreciated that the steps of operation should be construed to be complementary to the preceding description of the instrument enabling the phase and amplitude difference compensation. Particularly, component terms and numerals in preceding figures are re-used in the following description. FIGS. 1-4 are therefore continuously referred to.

According to FIG. 5, a dual mode calibration session employing the above disclosed instrument is illustrated. When a calibration session is initiated by an operator, in step 501, the NDT/NDI instrument is instructed to generate waveforms of the first frequency and the second frequency, waveform-1 and waveform-2, respectively. The waveforms are defined in the preceding description and generated by waveform generators 10.

In step 502, the two generated waveforms of the predetermined frequencies are added by adder 20 and are converted to analog signals in step 503 by DAC 30. In step 504, the resulting combined analog signals of frequency 1 and frequency 2 are fed to transmitter 50 and further to test object 55, and with the subsequent responding signals fed into differential amplifier and analog receiving circuit 60 in step 505.

Continuing with FIG. 5, on the other hand, in step 506 (506*a* and 506*b*) two null waveforms, null waveform-1 and null waveform-2 are generated by two null waveform generators 120-1 and 120-2 according the phase and amplitude difference in the specific calibration session. The null waveforms are added in step 507 and are further converted to analog nulling signals by DAC 150 in step 508.

In step 510, the analog nulling signals are used to subtract the resulting analog responding signals obtained in step 505. In step 511, the subsequent analog signals are digitized to ADC data 140 by ADC 70. In step 512, differences in phase and amplitude are detected by detector 80 by comparing the ADC data 140 with the generated waveforms of frequency 1 and frequency 2 resulted from step 501. The comparison results in pairs of values represented by corresponding real value X and real value Y and stored in memories in step 513 (513*a* and 513*b*). Real value X and Y are quantified representation of phase and amplitude differences in the corresponding waveform, and is used to instruct null waveform generator 120 to generate corresponding null waveforms back in step 506.

Although the present invention has been described in relation to particular exemplary embodiments thereof, many other variations and modifications and other uses will become apparent to those skilled in the art. It is preferred, therefore, that the present invention not be limited by the specific disclosure. For example, the scope of the present disclosure may be applied to a wide range of probes such as, but not limited to Eddy Current, Bond Testing and Hall-Effect (Magnetic) single element, multi-element, and array probes.

What is claimed is:

1. An apparatus operable for conducting non-destructive inspection (NDT/NDI) of a test object, comprising:
   an inspection probe with associated probe circuitry configured to generate detecting signals causing the test object to affect the characteristics of responding signals produced in response to the detecting signals, wherein the detecting signals possess a first frequency;
   a receiving, analyzing and displaying NDT/NDI instrument configured to receive, analyze and display the responding signals,
   wherein the NDT/NDI instrument further comprises:
   an analog to digital converter for converting the received responding signals from analog responding signals to digital responding signals represented by a responding signal waveform; and
   at least a first waveform detecting and generating circuit configured to generate a waveform of the first frequency, wherein the detecting and generating circuit is also configured to detect phase and amplitude differences between the responding signal waveform and the generated waveform of the first frequency.

2. The apparatus of claim 1, wherein the NDT/NDI instrument further comprises a digital null circuit including:
   at least a first null waveform generator configured to generate a first compensating waveform nulling the phase and amplitude differences according to detected phase and amplitude differences; and
   a digital to analog converter configured to convert the first compensating waveform from a digital to an analog compensating waveform and to feed the same to a subtracting circuit to cancel the effect of phase and amplitude differences.

3. The apparatus of claim 2, wherein the waveform detecting and generating circuit includes at least one phase and amplitude detector.

4. The apparatus of claim 2, wherein the waveform detecting and generating circuit includes:
   a first phase and amplitude detector generating a real value X, the real value X being stored in a real value memory; and
   a second phase and amplitude detector generating an imaginary value Y, the imaginary value Y being stored in an imaginary memory, wherein the value X and the value Y collectively provide quantified information on the phase and amplitude differences, based on which the first compensating waveform generator generates the first compensating waveform.

5. The apparatus of claim 2, wherein the NDT/NDI instrument further comprises:
   at least a second waveform detecting and generating circuit configured to generate a second digitally generated waveform of a second frequency,
   wherein the second detecting and generating circuit is also configured to detect the phase and amplitude differences between the responding signal waveform and the generated waveform of the second frequency,
   a detecting circuit adder by which the generated waveform of the first frequency and the generated waveform of the second frequency are added together to produce a combined generated waveform which is later converted to generate analog signals to be fed back to the probe circuitry,
   at least a second null waveform generator generating a second compensating waveform of a second frequency nulling the phase and amplitude differences, and,
   a null circuit adder by which the first compensating waveform and the second compensating waveform are added together to produce a combined compensating waveform, and
   a digital to analog converter configured to convert the combined compensating waveform to analog compensating waveform and to feed the same to a subtracting circuit to cancel the effect of the phase and amplitude differences.

6. The apparatus of claim 5, wherein the first and the second waveform detecting and generating circuits each includes at least one phase and amplitude detector.

7. The apparatus of claim 5, wherein the first the second waveform detecting and generating circuit include:
   a first phase and amplitude detector generating a first real value X, the first real value X being stored in a real value memory;
   a second phase and amplitude detector generating a first imaginary value Y, the first imaginary value Y being stored in an imaginary memory, wherein the first value X and the first value Y collectively provide quantified information on the phase and amplitude differences, based on which the first compensating waveform generator generating the first compensating waveform; and
   wherein the second waveform detecting and generating circuit includes:
   a third phase and amplitude detector generating a second real value X, the second real value X being stored in a real value memory;
   a fourth phase and amplitude detector generating a second imaginary value Y, the second imaginary value Y being stored in an imaginary memory, wherein the second value X and the second value Y collectively provide quantified information on the phase and amplitude differences, based on which the second compensating waveform generator is configured to generate the second compensating waveform.

8. The apparatus of claim 1, wherein the NDT/NDI instrument further comprises a digital null circuit including:
   at least a first null waveform generator configured to generate a pair of orthogonal null waveforms, the amplitudes and phases of the orthogonal waveforms being adjusted by corresponding amplitude controls,
   a null adder that adds the orthogonal null waveforms to form the first compensating waveform nulling the phase and amplitude differences according to detected phase and amplitude differences; and
   a digital to analog converter configured to convert the first compensating waveform from digital to analog compensating waveform and feeding the same to a subtracting circuit to cancel the effect of the phase and amplitude differences.

9. The apparatus of claim 1, wherein the detecting signals are in the form of eddy current energy.

10. The apparatus of claim 1, wherein the detecting signals are in the form of acoustic energy wherein the acoustic energy is in an energy form of one of the following: sound, vibration, ultrasound and infrasound.

11. The apparatus of claim 1, wherein the detecting signals are in the form of magnetic energy.

12. The apparatus of claim 1, wherein the waveform generator is a direct digital synthesizer.

13. A method of detecting and compensating phased and amplitude differences including a probe generating detecting signals causing a test object to affect characteristics responding signals, in response to the detecting signals, the detecting signals possess a first frequency, the method comprising the steps of:

a. digitizing the responding signals to a digitized responding waveform using an analog to digital converter;
 b. generating a digitally generated waveform of the first frequency using a digital waveform generator;
 c. converting the generated waveform of the first frequency to generated analog signals of the first frequency and feeding the same back to the probe;
 d. detecting and quantifying differences in phase and amplitude between the responding waveform and the generated waveform of the first frequency using a phase and amplitude detector;
 e. generating a null waveform according to the quantified differences in phase and amplitude using a null waveform generator and converting the null waveform to analog null signals using a digital to analog converter; and
 f. nulling the phase and amplitude differences by subtracting the analog null signals from the inspection signals which includes the generated analog signals of the first frequency.

14. The method of claim 13, wherein the detecting signals are in the form of eddy current energy.

15. The method of claim 13, wherein the detecting signals are in the form of acoustic energy, wherein the acoustic energy is in an energy form of one of the following: sound, vibration, ultrasound and infrasound.

16. The method of claim 13, wherein the detecting signals are in the form of magnetic energy.

17. The method of claim 13, wherein the waveform generator is a direct digital synthesizer.

18. A detection and compensation circuitry for detecting and compensating phase and amplitude differences for an NDT/NDI inspection instrument with an associated probe configured to generate detecting signals causing a test object to affect the characteristics of responding signals in responding to the detecting signals, the detecting signals possess a first frequency, the detection and compensation circuitry comprising:
 an analog to digital converter for converting the received responding signals from analog responding signals to digital responding signals represented by a responding signal waveform;
 at least a first waveform detecting and generating circuit configured to generate a digitally generated waveform of the first frequency, wherein the detecting and generating circuit is also configured to detect phase and amplitude differences between the responding signal waveform and the generated waveform of the first frequency;
 at least a first null waveform generator for generating a first compensating waveform nulling the phase and amplitude differences according to detected phase and amplitude differences; and
 a digital to analog converter for converting the first compensating waveform from a digital to an analog compensating waveform and feeding the same to a subtracting circuit to cancel the effect of the phase and amplitude differences.

19. The apparatus of claim 18, wherein the detecting signals are in the form of eddy current energy.

20. The apparatus of claim 18, wherein the detecting signals are in the form of acoustic energy, wherein the acoustic energy is an energy form of one of the following: sound, vibration, ultrasound and infrasound.

21. The apparatus of claim 18, wherein the detecting signals are in the form of magnetic energy.

\* \* \* \* \*